United States Patent
Cao et al.

(10) Patent No.: US 11,291,420 B2
(45) Date of Patent: Apr. 5, 2022

(54) X-RAY IMAGING SYSTEM AND METHOD OF X-RAY IMAGE TRACKING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 170 days.

(21) Appl. No.: 16/742,791

(22) Filed: Jan. 14, 2020

(65) Prior Publication Data

US 2020/0150288 A1     May 14, 2020

Related U.S. Application Data

(63) Continuation of application No. PCT/CN2017/094456, filed on Jul. 26, 2017.

(51) Int. Cl.
*A61B 6/00* (2006.01)
*A61N 5/10* (2006.01)
(Continued)

(52) U.S. Cl.
CPC .............. *A61B 6/4266* (2013.01); *A61B 6/42* (2013.01); *A61B 6/4208* (2013.01);
(Continued)

(58) Field of Classification Search
CPC ....... A61B 6/42; A61B 6/4208; A61B 6/4233; A61B 6/4241; A61B 6/4266; A61B 6/44;
(Continued)

(56) References Cited

U.S. PATENT DOCUMENTS

| | | | | |
|---|---|---|---|---|
| 5,278,887 A | * | 1/1994 | Chiu | ........................ G21K 1/10 378/156 |
| 5,282,254 A | * | 1/1994 | Chiu | ........................ A61B 6/06 378/159 |

(Continued)

FOREIGN PATENT DOCUMENTS

| | | |
|---|---|---|
| CN | 102858249 A | 1/2013 |
| DE | 102012203291 A1 | 3/2013 |

(Continued)

*Primary Examiner* — Allen C. Ho
(74) *Attorney, Agent, or Firm* — IPro, PLLC; Qian Gu

(57) ABSTRACT

Disclosed herein is a method for image tracking using an X-ray imaging system during an interventional radiology procedure on a human or an animal. The method may comprise acquiring a first image of an object inside a human or an animal with a first X-ray detector of the X-ray imaging system; acquiring a second image of the object with the X-ray imaging system during the interventional radiology procedure, at a time later than acquiring the first image; determining a displacement of the first X-ray detector based on the first image and the second image; moving the first X-ray detector by the displacement, with an actuator of the X-ray imaging system. The X-ray imaging system comprises the first X-ray detector, the second X-ray detector and the actuator. A spatial resolution of the first X-ray detector is higher than a spatial resolution of the second X-ray detector.

27 Claims, 10 Drawing Sheets

(51) Int. Cl.
   *G01T 1/20* (2006.01)
   *G01T 1/24* (2006.01)
   *G01T 1/29* (2006.01)
(52) U.S. Cl.
   CPC .......... *A61B 6/4233* (2013.01); *A61B 6/4241* (2013.01); *A61B 6/44* (2013.01); *A61B 6/4405* (2013.01); *A61B 6/4411* (2013.01); *A61B 6/4452* (2013.01); *A61B 6/4458* (2013.01); *A61B 6/482* (2013.01); *A61B 6/486* (2013.01); *A61B 6/487* (2013.01); *A61B 6/504* (2013.01); *A61B 6/508* (2013.01); *A61B 6/54* (2013.01); *A61B 6/547* (2013.01); *A61N 5/1001* (2013.01); *G01T 1/2014* (2013.01); *G01T 1/241* (2013.01); *G01T 1/2914* (2013.01)
(58) Field of Classification Search
   CPC ... A61B 6/4405; A61B 6/4411; A61B 6/4452; A61B 6/4458; A61B 6/486; A61B 6/487; A61B 6/504; A61B 6/508; A61B 6/54; A61B 6/547; A61B 6/4429; A61B 6/482; A61B 6/484; A61B 6/542; A61B 6/545
   USPC ..................... 378/62, 98.8, 98.9, 98.11, 189; 250/370.09
   See application file for complete search history.

(56) References Cited

U.S. PATENT DOCUMENTS

| | | | | |
|---|---|---|---|---|
| 5,369,678 A | * | 11/1994 | Chiu | A61B 6/06 378/152 |
| 6,285,739 B1 | * | 9/2001 | Rudin | A61B 6/4233 378/62 |
| 6,463,121 B1 | * | 10/2002 | Milnes | A61B 6/469 378/62 |
| 6,592,259 B2 | * | 7/2003 | Crain | A61B 6/107 378/196 |
| 6,637,936 B2 | * | 10/2003 | Crain | A61B 6/107 378/162 |
| 7,170,974 B2 | * | 1/2007 | Groh | A61B 6/00 378/98.8 |
| 7,522,701 B2 | * | 4/2009 | Jensen | A61B 6/481 378/162 |
| 7,634,308 B2 | * | 12/2009 | Ogawa | A61B 6/481 378/196 |
| 7,734,007 B2 | * | 6/2010 | Kargar | A61B 6/542 378/8 |
| 7,798,708 B2 | * | 9/2010 | Erhardt | G03B 42/042 378/191 |
| 8,295,573 B2 | * | 10/2012 | Bredno | A61B 6/507 382/130 |
| 9,700,209 B2 | * | 7/2017 | Florent | A61B 5/0037 |
| 9,724,061 B2 | * | 8/2017 | Hyung | A61B 6/503 |
| 10,610,181 B2 | * | 4/2020 | Chen | G06T 7/246 |
| 10,869,642 B2 | * | 12/2020 | Nempont | G06T 7/246 |
| 10,891,763 B2 | * | 1/2021 | Hoornaert | G06T 7/38 |
| 11,026,648 B2 | * | 6/2021 | Mielekamp | A61B 6/469 |
| 2005/0169426 A1 | | 8/2005 | Groh et al. | |
| 2006/0039537 A1 | | 2/2006 | Strobel | |
| 2008/0125649 A1 | | 5/2008 | Meyer et al. | |
| 2015/0342556 A1 | | 12/2015 | Van Dijk | |

FOREIGN PATENT DOCUMENTS

| | | |
|---|---|---|
| JP | 2011004966 A | 1/2011 |
| JP | 2014217615 A | 11/2014 |
| JP | 2015150206 A | 8/2015 |
| WO | 2016161542 A1 | 10/2016 |

\* cited by examiner

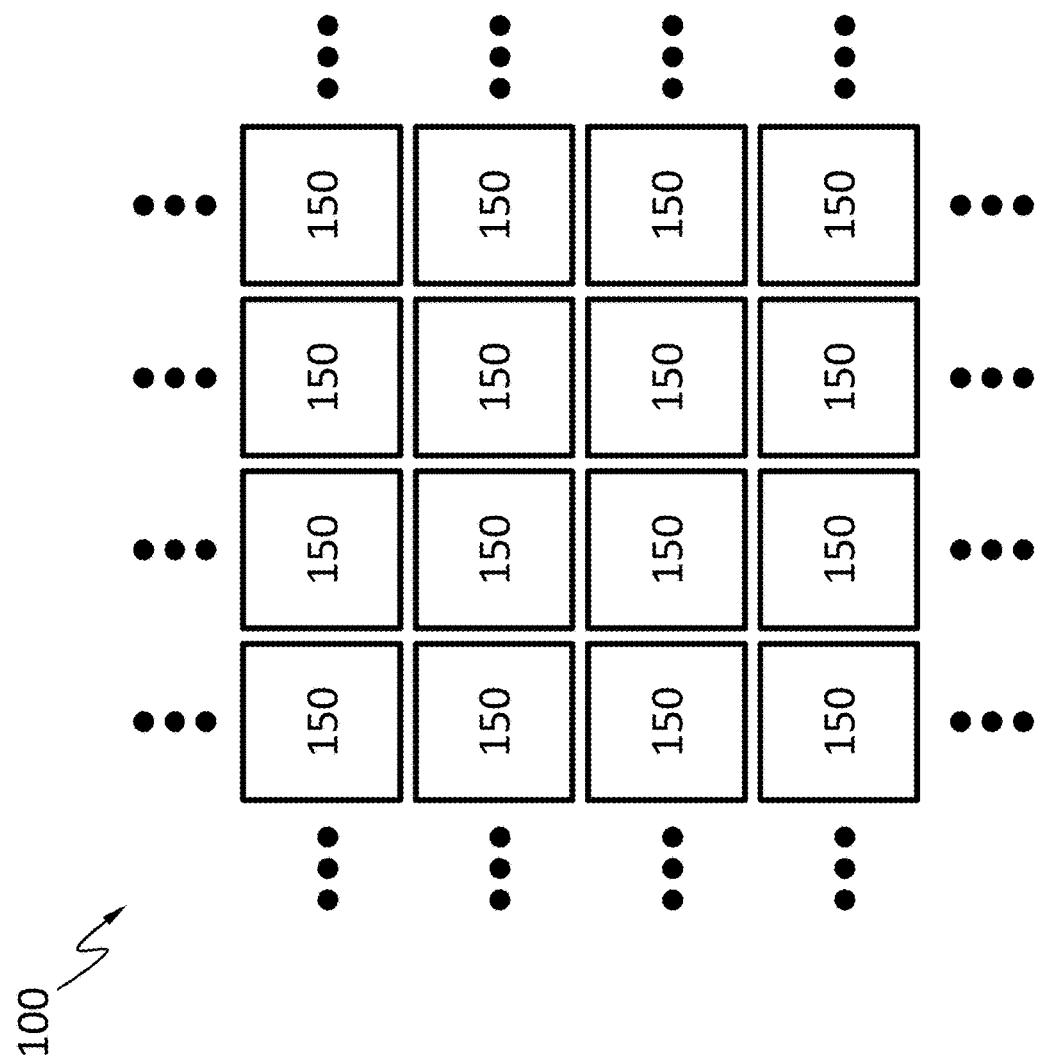

X-RAY IMAGING SYSTEM AND METHOD OF X-RAY IMAGE TRACKING

TECHNICAL FIELD

The disclosure herein relates to a method of X-ray image tracking, particularly relates a method of X-ray image tracking with an X-ray imaging system comprising two X-ray detectors.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., do not require post-exposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is a method comprising: acquiring a first image of an object inside a human or animal with a first X-ray detector of an X-ray imaging system during an interventional radiology procedure on the human or animal; acquiring a second image of the object with the X-ray imaging system during the interventional radiology procedure, at a time later than acquiring the first image; determining a displacement of the first X-ray detector based on the first image and the second image; moving the first X-ray detector by the displacement, with an actuator of the X-ray imaging system; wherein the X-ray imaging system comprises the first X-ray detector, a second X-ray detector, the actuator; wherein the first X-ray detector and the second X-ray detector are each capable of acquiring an image; wherein a spatial resolution of the first X-ray detector is higher than a spatial resolution of the second X-ray detector; wherein a detection area of the first X-ray detector is smaller than a detection area of the second X-ray detector; wherein the actuator is configured to move the first X-ray detector relative to the second X-ray detector in one or more directions; wherein one of the one or more directions is not perpendicular to an imaging plane of the second X-ray detector.

According to an embodiment, the object is a portion of a catheter, a portion of a probe, a portion of a needle, or a portion of a wire.

According to an embodiment, the object comprises a marker configured to show contrast in the first image and the second image.

According to an embodiment, determining the displacement comprises subtracting a background from the first image or the second image, or comprises determining a differential between the first image and second image.

According to an embodiment, the second image is taken by the first X-ray detector.

According to an embodiment, the second image is taken by the second X-ray detector.

According to an embodiment, the method of claim further comprises: taking images with the second X-ray detector to determine an area of interest containing the object; moving the first X-ray detector to have the detection area of the first X-ray detector overlap with the area of interest.

According to an embodiment, determining the area of interest is done by processing the images taken with the second X-ray detector.

According to an embodiment, the method further comprises: making a composite image by combining an image formed by the first X-ray detector and another image formed by the second X-ray detector.

According to an embodiment, the first X-ray detector is configured to count photons of X-ray incident thereon.

According to an embodiment, the first X-ray detector is pixelated.

According to an embodiment, the first X-ray detector comprises cadmium telluride (CdTe) or cadmium zinc telluride (CZT).

According to an embodiment, the second X-ray detector comprises a scintillator.

According to an embodiment, the actuator comprises a material that is selected from a group consisting of aluminum, aluminum composite, carbon fiber and a combination thereof.

According to an embodiment, the actuator comprises a robotic arm.

According to an embodiment, the actuator comprises a first rail and a second rail; wherein the first X-ray detector is configured to slide along the first rail; and wherein the first rail is configured to slide along the second rail, wherein the first and second rails are not parallel.

According to an embodiment, the first X-ray detector comprises: an X-ray absorption layer comprising an electrode; a first voltage comparator configured to compare a voltage of the electrode to a first threshold; a second voltage comparator configured to compare the voltage to a second threshold; a counter configured to register a number of X-ray photons absorbed by the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the first X-ray detector further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the first X-ray detector further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

According to an embodiment, the first X-ray detector does not comprise a scintillator.

Disclosed herein is a computer program product comprising a non-transitory computer readable medium having instructions recorded thereon, the instructions when executed by a computer implementing a method comprising: acquiring a first image of an object inside a human or animal with a first X-ray detector of an X-ray imaging system during an interventional radiology procedure on the human or animal; acquiring a second image of the object with the X-ray imaging system during the interventional radiology procedure, at a time later than acquiring the first image; determining a displacement of the first X-ray detector based on the first image and the second image; moving the first X-ray detector by the displacement, with an actuator of the X-ray imaging system; wherein the X-ray imaging system comprises the first X-ray detector, a second X-ray detector, the actuator; wherein the first X-ray detector and the second X-ray detector are each capable of acquiring an image; wherein a spatial resolution of the first X-ray detector is higher than a spatial resolution of the second X-ray detector; wherein a detection area of the first X-ray detector is smaller than a detection area of the second X-ray detector; wherein the actuator is configured to move the first X-ray detector relative to the second X-ray detector in one or more directions; wherein one of the one or more directions is not perpendicular to an imaging plane of the second X-ray detector.

According to an embodiment, the object is a portion of a catheter, a portion of a probe, a portion of a needle, or a portion of wire.

According to an embodiment, the object comprises a marker configured to show contrast in the first image and the second image.

According to an embodiment, determining the displacement comprises subtracting a background from the first image or the second image, or comprises determining a differential between the first image and second image.

According to an embodiment, the second image is taken by the first X-ray detector.

According to an embodiment, the second image is taken by the second X-ray detector.

According to an embodiment, the method further comprises: taking images with the second X-ray detector to determine an area of interest; moving the first X-ray detector to have the detection area of the first X-ray detector overlap with the area of interest.

According to an embodiment, determining the area of interest is done by processing the images taken with the second X-ray detector.

According to an embodiment, the method further comprises: making a composite image by combining an image formed by the first X-ray detector and another image formed by the second X-ray detector.

According to an embodiment, the first X-ray detector is configured to count photons of X-ray incident thereon.

According to an embodiment, the first X-ray detector is pixelated.

According to an embodiment, the first X-ray detector comprises cadmium telluride (CdTe) or cadmium zinc telluride (CZT).

According to an embodiment, the second X-ray detector comprises a scintillator.

According to an embodiment, the actuator comprises a material that is selected from a group consisting of aluminum, aluminum composite, carbon fiber and a combination thereof.

According to an embodiment, the actuator comprises a robotic arm.

According to an embodiment, the actuator comprises a first rail and a second rail; wherein the first X-ray detector is configured to slide along the first rail; and wherein the first rail is configured to slide along the second rail, wherein the first and second rails are not parallel.

According to an embodiment, the first X-ray detector comprises: an X-ray absorption layer comprising an electrode; a first voltage comparator configured to compare a voltage of the electrode to a first threshold; a second voltage comparator configured to compare the voltage to a second threshold; a counter configured to register a number of X-ray photons absorbed by the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the first X-ray detector further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the first X-ray detector further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

According to an embodiment, the first X-ray detector does not comprise a scintillator.

BRIEF DESCRIPTION OF FIGURES

FIG. 5 schematically shows an X-ray detector, as an example.

DETAILED DESCRIPTION

Figure 1:
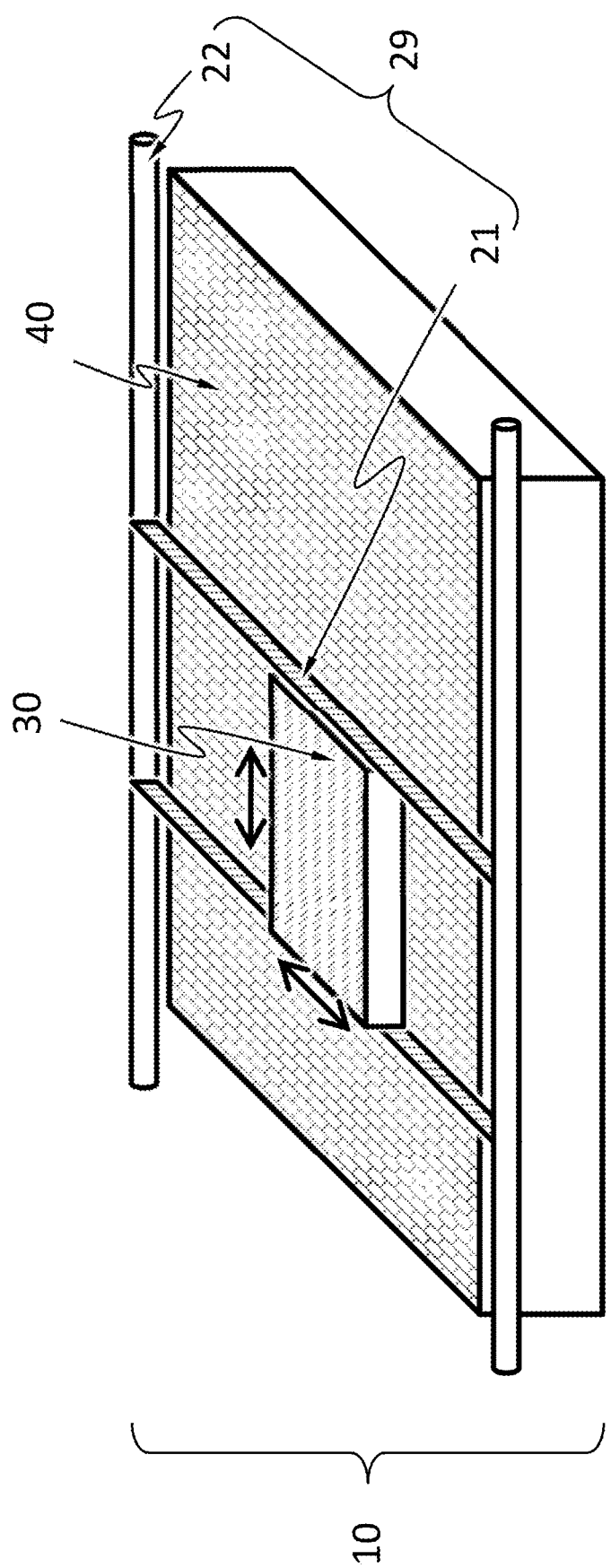
FIG. 1 schematically shows an X-ray imaging system suitable for detecting X-ray, according to an embodiment.

FIG. 1 schematically shows an X-ray imaging system 10 suitable for detecting X-ray comprises a first X-ray detector 30, and a second X-ray detector 40, according to an embodiment. The first X-ray detector 30 is configured to move relative to the second X-ray detector 40. A spatial resolution of the first X-ray detector 30 is higher than a spatial resolution of the second X-ray detector 40. The first X-ray detector 30 and the second X-ray detector 40 are each capable of forming an image. The first X-ray detector 30 generally may have a detection area that is smaller than a detection area of the second X-ray detector 40. As used herein, a detection area of an X-ray detector is the area thereof that is capable of detecting X-ray.

The first X-ray detector 30 may be any suitable X-ray detector, including but not limited to an X-ray detector 100 shown in FIG. 5 and FIG. 6A-FIG. 6C below. The first X-ray detector 30 may count photons of X-ray incident thereon. The first X-ray detector 30 may be pixelated. The first X-ray detector 30 may comprise cadmium telluride (CdTe) or cadmium zinc telluride (CZT). Semiconductors CdTe and CZT have emerged as the material of choice for room temperature detection of hard X-rays, and they provide high spatial and temporal resolution in imaging. One application of such X-ray detector with a first CZT detector is medical imaging in medical operations such as heart surgeries. In an embodiment, the second X-ray detector 40 may have a scintillator; alternatively the second X-ray detector 40 may be a semiconductor X-ray detector capable of photo counting, but with a lower resolution than the first X-ray detector 30.

Figure 2:
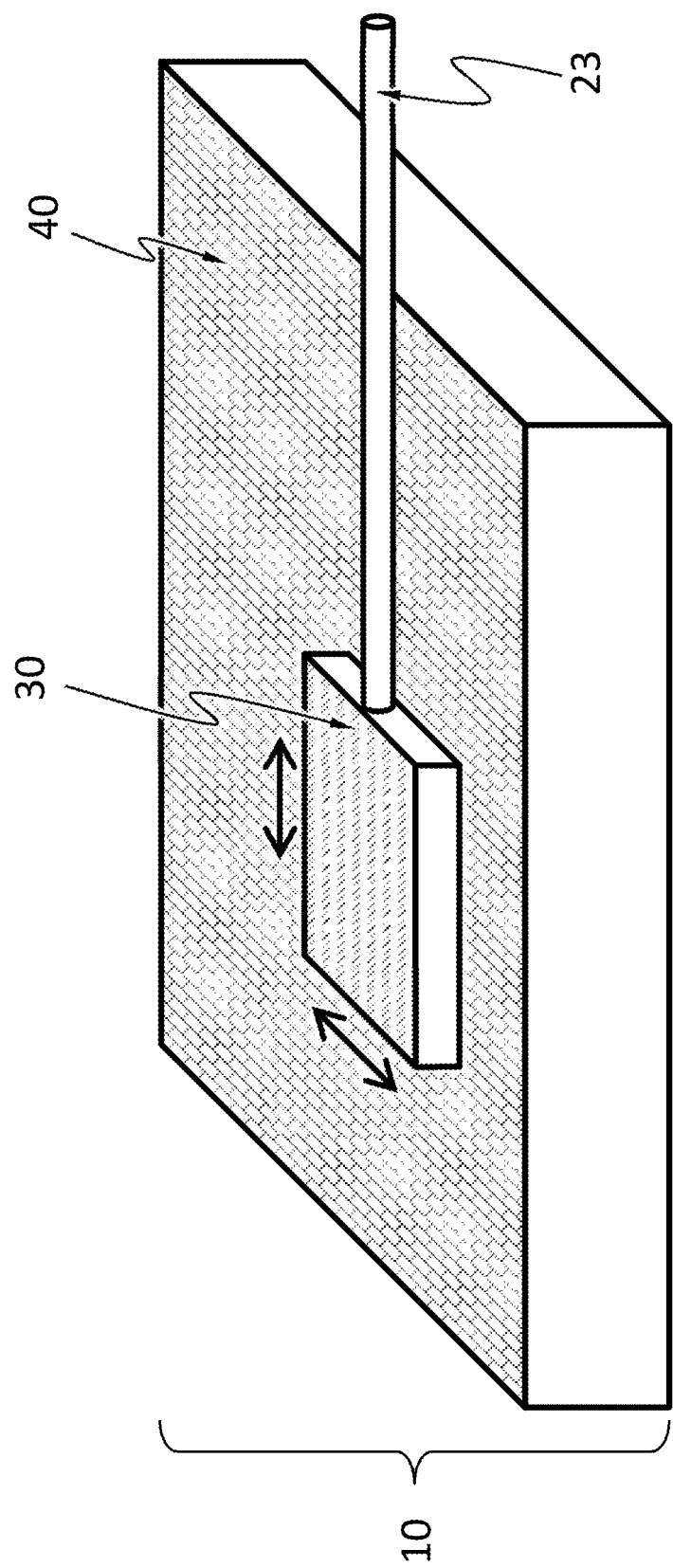
FIG. 2 schematically shows a variant of the X-ray imaging system, according to an embodiment.

In an embodiment, the first X-ray detector 30 may be on top of the second X-ray detector 40 in an overlay fashion as shown in FIGS. 1 and 2. Alternatively, the first X-ray detector 30 may be on a side of the second X-ray detector 40.

The X-ray imaging system 10 may be exposed to an X-ray source. In an embodiment, the X-ray imaging system 10 may further comprise a special filter for X-rays from the X-ray source, so that only the detection area corresponding to the X-ray first detector 30 may receive enough X-ray dose, while the rest of the detection area may receive only reduced X-ray dose. The X-ray imaging system 10 may reduce X-ray dose received by the patient. In an embodiment, the filter may have a rectangle hole in the middle to allow the X-ray to pass through, and the rectangle hole is aligned with the detection area corresponding to the first X-ray detector 30; the rest of the filter is made of copper of a predetermined thickness that may reduce the X-ray dose.

In an embodiment, a frame rate of the first X-ray detector 30 is higher than a frame rate of the second X-ray detector 40; such an X-ray imaging system 10 may work as a DSA detector. For example, the first X-ray detector 30 can work at 30 frames per second, while the second X-ray detector 40 only work at 10 frames per second.

The X-ray imaging system 10 may further comprise an actuator 29 configured to move the first X-ray detector 30 relative to the second X-ray detector 40 in one or more directions; and at least one of the one or more directions is not perpendicular to an imaging plane of the second X-ray detector 40. As used herein, an imaging plane is the plane from which an X-ray detector takes image from. When the first X-ray detector 30 and the second X-ray detector 40 are used to take images of an object, the first X-ray detector 30 is often used to take a high resolution image on an area of interest on the object, and the second X-ray detector 40 is often used to take a low resolution background image on the overall object or a larger area of the object that comprises the area of interest. In such an example, the imaging planes of the first X-ray detector 30 and the second X-ray detector 40 are the same or are in close proximity, and the first X-ray detector 30 is moved approximately parallel to the second X-ray detector 40.

In an embodiment, the actuator 29 comprises a material that has low X-ray absorption, and the material may be selected from a group consisting of aluminum, aluminum composite, carbon fiber and a combination thereof. Such material selection ensures the actuator 29 is generally not shown in the X-ray imaging results. The actuator 29 may be moved out of the view of the second X-ray detector 40.

In an embodiment, as shown in FIG. 1, the actuator 29 comprises a first rail 21 and a second rail 22; the first X-ray detector 30 may slide along the first rail 21; and the first rail 21 may slide along the second rail 22 so that the first X-ray detector 30 is moved relative to the second X-ray detector 40. The first rail 21 and the second rail 22 are not parallel. The first rail 21 and the second rail 22 may be at an angle that is 90 degrees or not 90 degrees. The directions of the first rail 21 and the second rail 22 may or may not be parallel to the edges of the second X-ray detector 40; therefore the directions of the edges of the first X-ray detector 30 may or may not be parallel to the edges of the second X-ray detector 40.

FIG. 2 schematically shows a variant of the X-ray imaging system 10, where the actuator 29 comprises a robotic arm 23 that connects to the first X-ray detector 30, according to an embodiment. When in use, the robotic arm 23 moves the first X-ray detector 30 relative to the second X-ray detector 40 to an area of interest. The actuator 29 may have other forms that function to move the first X-ray detector 30 relative to the second X-ray detector 40.

Figure 3:
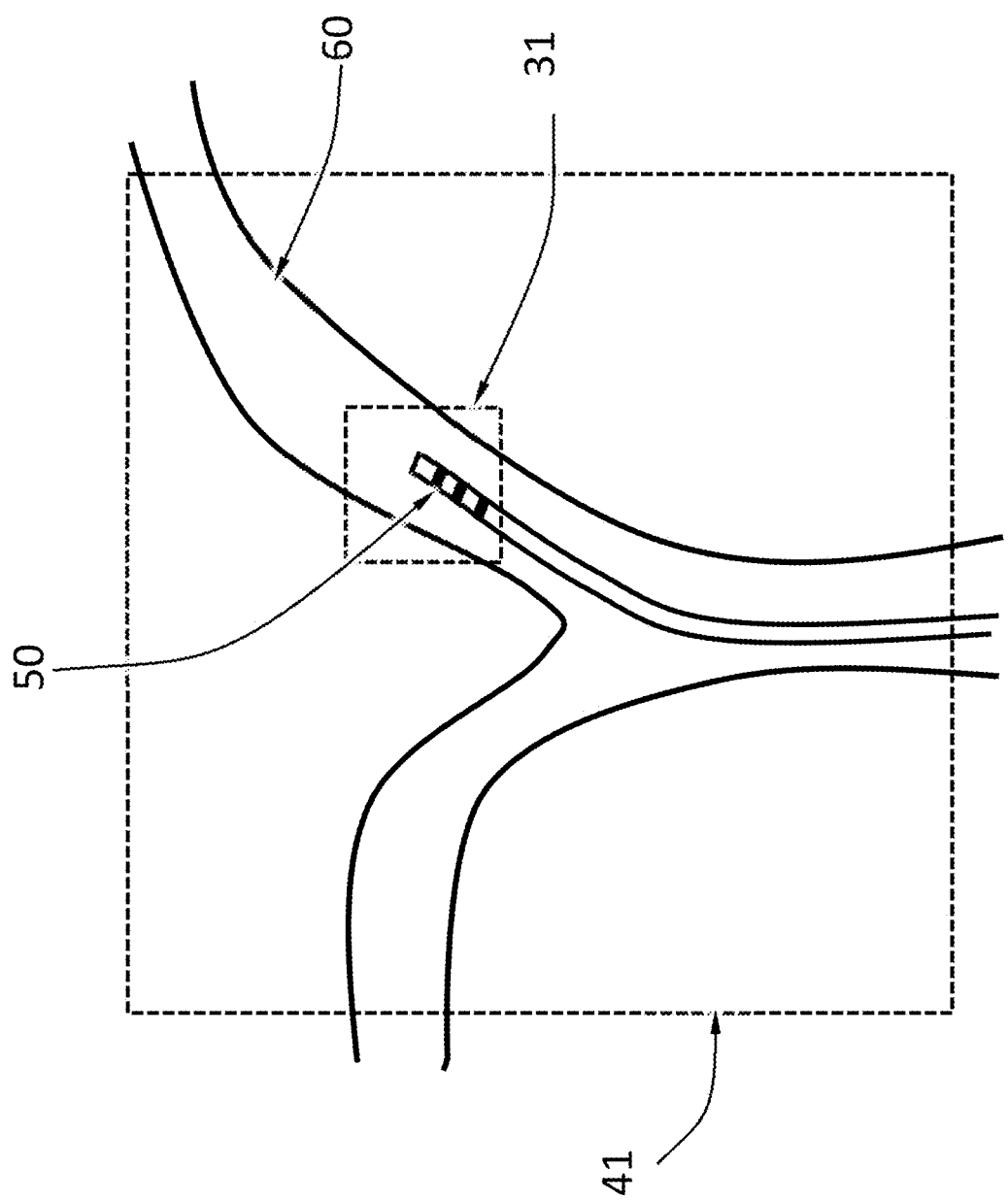
FIG. 3 schematically shows using the X-ray imaging system for image tracking during an interventional radiology procedure on a human or animal, according to an embodiment.

FIG. 3 schematically shows using the X-ray imaging system 10 for image tracking during an interventional radiology procedure on a human or animal, according to an embodiment. The human or animal body may be exposed to a continuous or intermittent source of X-rays from an X-ray source. The second X-ray detector 40 with a detection area 41 may be configured to take images of an area containing an object 50 and surroundings thereof inside the human or animal. The first X-ray detector 30 with a detection area 31 may be configured to follow the object 50 within the detection area 41 and take images of the object 50 with higher resolution than the images taken by the second X-ray detector 40.

The interventional radiology procedure may provide image-guided diagnosis and treatment of disease, and may cover a broad range of procedures such as endovascular surgery, needle biopsies, radiofrequency ablation, etc.

The object 50 may be a portion of a small medical instrument such as catheter, probe, needle, wire, tube, or any other specialized tool. The object 50 may be inserted through a small surgical cut into the human or animal to perform a procedure. The object 50 may have varying properties (e.g., length, material, shape) allowing for different functions such as destroying tumors, treating diseased blood vessels, stopping bleeds, stopping blood clot migration, etc. In an embodiment, the object 50 may comprise a marker configured to show contrast in the images taken by the first X-ray detector 30 and the second X-ray detector 40.

In the example of FIG. 3, the object 50 may be an end of a catheter, which may be inserted percutaneously into a blood vessel 60. The catheter comprises a marker that comprises high-contrast stripes near the end of the catheter. The second X-ray detector 40 takes images of a portion of the blood vessel 60 in which the end of the catheter moves. The first X-ray detector 30 tracks and takes images of the end of the catheter.

Figure 4:
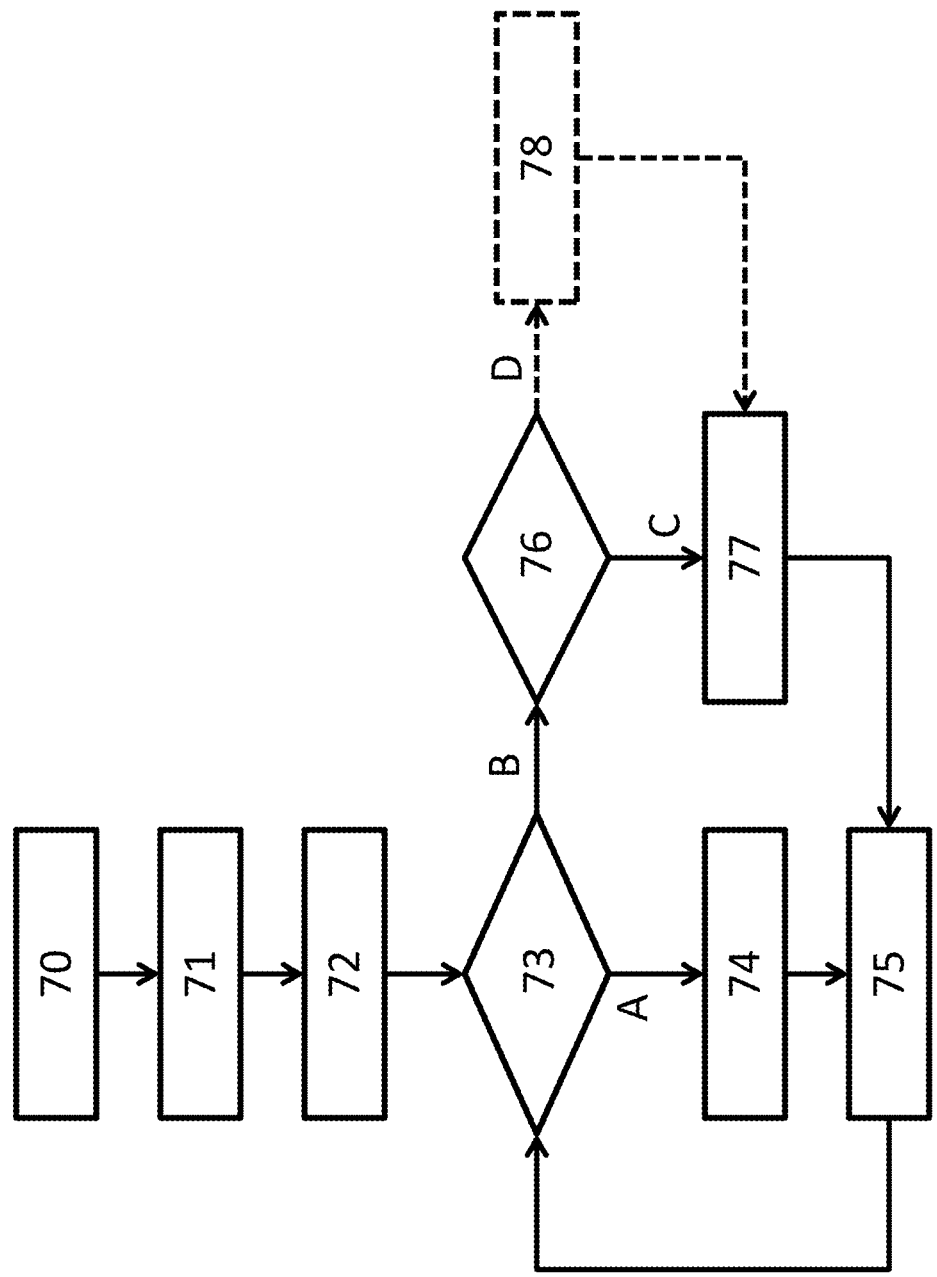
FIG. 4 shows a flow chart for a method suitable for image tracking using the X-ray imaging system as shown in FIG. 3, according to an embodiment.

FIG. 4 shows a flowchart for a method suitable for image tracking using the X-ray imaging system 10 as shown in FIG. 3, according to an embodiment.

In step 70, an image is taken at $t_1$ and another image is taken at $t_2$, e.g., with the second X-ray detector 40. A time t with a larger numerical subscript is no earlier than a time with a smaller numerical subscript (i.e., $t_1 \leq t_2 \leq t_3 \leq t_4$, etc.). The images taken at $t_1$ and $t_2$ overlap with a detection region of interest (e.g., containing the portion of the blood vessel 60 in FIG. 3).

In an embodiment, the image taken at $t_1$ may or may not have the object 50 present in the detection region of interest. The image taken at $t_2$ may be an image taken after the object 50 enters into the same detection region of interest thus having the object 50 present therein. In an embodiment, the second X-ray detector 40 may take images at a specific frame rate (e.g., 3 to 50 frames per second) and each of the images has a time stamp (e.g., $t_1$, $t_2$, etc.). The images taken at $t_1$ and $t_2$ may or may not be consecutive images taken by the second X-ray detector 40.

In step 71, a position or other relevant information of the object 50 at $t_2$ is determined by processing the images taken at $t_1$ and $t_2$, and a displacement of the first X-ray detector 30 is calculated based the position of object 50 at $t_2$. The displacement may equal or approximate the displacement in the imaging plane from the location of the first X-ray detector 40 at $t_2$ to the location of the object 50 at $t_2$.

Image processing may be done by various techniques used for object recognition and tracking. In an embodiment, processing the images may comprise subtracting a background (e.g., the image at $t_1$ if the object 50 is not present therein) from a current image (e.g., the image taken at $t_2$). Presumably, the difference between the current image (e.g., the image at $t_2$) and the background may correspond to the object 50 and may be computed to identify the object 50. In an embodiment, processing the images may comprise determining a differential between a current image (e.g., the image at $t_2$) and a previous image (e.g., the image at $t_1$). The absolute difference between the current image and the previous image may be used divide the current image into changed and unchanged regions. The changed region may associate with the object 50 and may be further processed to identify the object 50. In an embodiment, features of the object 50 such as corner, edges or markers (e.g., the high-contrast marker on the end of the catheter in FIG. 3) may be used to describe the object 50. In other words, positions or other relevant information of the features (or points on the features) may be used to describe the position or other relevant information of the object 50. Matching the features in images may be performed to identify and track the object 50, and the feature matching may be done by finding a correlation score (or other matching criteria) of the features in an image (e.g., the image at $t_2$) with a value better than a tolerated value. The feature matching may be used together with background subtraction or image differential to improve accuracy and efficiency of object recognition and tracking during the image processing.

In step 72, the first X-ray detector 30 is relocated, e.g., with the actuator 29, by the displacement determined in step 71, and an image of the object 50 is taken at t3 with the first X-ray detector 30. The object 50 may move during the time period between t2 and t3 (i.e., the time period of imaging processing and relocating the first X-ray detector 30). In an embodiment, the movement of the object 50 during the time period between t2 and t3 is small enough so that the object 50 is still within the detection area 31 of the first X-ray detector 30 at t3 if the first X-ray detector 30 is moved to the position of the object 50 at t2. In another embodiment, a motion prediction of the object 50 during the time period between t2 and t3 may be carried out and taken into account during the displacement calculation in step 71 to ensure that the object 50 falls into the detection area 31 of the first X-ray detector 30 at t3.

In step 73, an image is taken at $t_4$ with the first X-ray detector 30, and the images taken at $t_3$ and $t_4$ are processed to check whether the object 50 is still within the detection area 31 of the first X-ray detector 30 at $t_4$. The imaging processing is carried out in a way similar to the way as described in step 71. When the object 50 is still within the detection area 31 of the first X-ray detector 30 at $t_4$, the flow may follow path A in FIG. 4 and move onto a step 74. When the object moves beyond the detection area 31 of the first X-ray detector 30 at $t_4$, the flow may follow path B in FIG. 4 and move onto a step 76.

In an embodiment, the first X-ray detector 30 may take images at a specific frame rate (e.g., 3 to 50 frames per second) and each of the images has a time stamp (e.g., $t_3$, $t_4$, etc.). The images taken at $t_3$ and $t_4$ may or may not necessarily consecutive images taken by the first X-ray detector 30. The frame rate of the first X-ray detector 30 may equal to or faster than the frame rate of the second X-ray detector 40.

In step 74, a position or other relevant information of the object 50 at $t_4$ is determined by processing the images at $t_3$ and $t_4$, and a displacement of the first X-ray detector 30 is calculated in a way similar to the way described in step 71. The displacement may equal or approximate to the displacement in the imaging plane from the location of the first X-ray detector 30 at $t_3$ to the location of the object 50 at $t_4$.

In step 75, the first X-ray detector 30 is relocated, e.g., with the actuator 29, by the displacement determined in step 74, an image of the object 50 is taken at the end of the relocation with the first X-ray detector 30, and the flow may return to step 73 if the tracking is not terminated or paused.

In step 76, an image at $t_5$ is taken with the second X-ray detector 40, and the images taken at $t_3$ and $t_5$ are processed to check whether the object 50 is within the detection area 41 of the second X-ray detector 40 at $t_5$. Time $t_5$ may equal or approximate $t_4$, and the time interval between $t_4$ and $t_5$ may depend on the frame rates of the first and second X-ray detectors 30 and 40. When the object 50 is within the detection area 41 of the second X-ray detector 40 at $t_5$, the flow may follow path C in FIG. 4 and move onto a step 77. When the object 50 moves beyond the detection area 41 of the second X-ray detector 40 at $t_5$ while the detection area 41 is smaller than the overall region of interest of an interventional radiology procedure, the flow may follow path D in FIG. 4 and move to step 78.

In step 77, a position or other relevant information of the object 50 at $t_5$ is determined by processing the image taken at $t_3$ by the first X-ray detector 30 and the image taken at $t_5$ by the second X-ray detector 40, and a displacement of the first X-ray detector 30 is calculated in a way similar to the way described in step 71. The displacement may equal or approximate to the displacement in the imaging plane from the location of the first X-ray detector 30 at $t_3$ to the location of the object 50 at $t_5$. Then the flow may return to step 75.

In optional step 78, the second X-ray detector 40 may be moved to search around the location of the object 50 at $t_3$. After the object 50 is located (e.g., by identifying the features of the object 50), the flow may return to step 77.

The steps 70-78 in FIG. 4 are for illustration purpose only. Details of the steps 70-78 may vary and some additional steps may be carried out, depending on the application needs and conditions of an interventional radiology procedure.

A method suitable for image tracking using the X-ray imaging system 10, such as the method illustrated in FIG. 4, may be implemented when executing some instructions by a computer program product on a computer. The computer program product may comprise a non-transitory computer readable medium having the instructions recorded thereon.

FIG. 5 schematically shows an X-ray detector 100, as an example. The X-ray detector 100 may be used as the first X-ray detector 30 or the second X-ray detector 40 in the X-ray imaging system 10 in FIG. 1 and FIG. 2. The X-ray detector 100 has an array of pixels 150. The array may be a rectangular array, a honeycomb array, a hexagonal array or any other suitable array. Each pixel 150 is configured to detect X-ray from an X-ray source incident thereon and may be configured measure a characteristic (e.g., the energy of the photons, the wavelength, and the frequency) of the X-ray. For example, each pixel 150 is configured to count numbers of photons incident thereon whose energy falls in a plurality of bins, within a period of time. All the pixels 150 may be configured to count the numbers of photons incident thereon within a plurality of bins of energy within the same period of time. Each pixel 150 may have its own analog-to-digital converter (ADC) configured to digitize an analog signal representing the energy of an incident photon into a digital signal. The pixels 150 may be configured to operate in parallel. For example, when one pixel 150 measures an incident photon, another pixel 150 may be waiting for a photon to arrive. The pixels 150 may not have to be individually addressable.

Figure 6A:
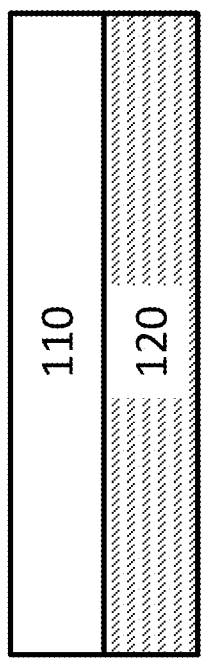
FIG. 6A schematically shows a cross-sectional view of the X-ray detector, according to an embodiment.

FIG. 6A schematically shows a cross-sectional view of the X-ray detector 100, according to an embodiment. The X-ray detector 100 may include an X-ray absorption layer 110 and an electronics layer 120 (e.g., an ASIC) for processing or analyzing electrical signals incident X-ray generates in the X-ray absorption layer 110. The X-ray detector 100 may or may not include a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray of interest.

Figure 6B:
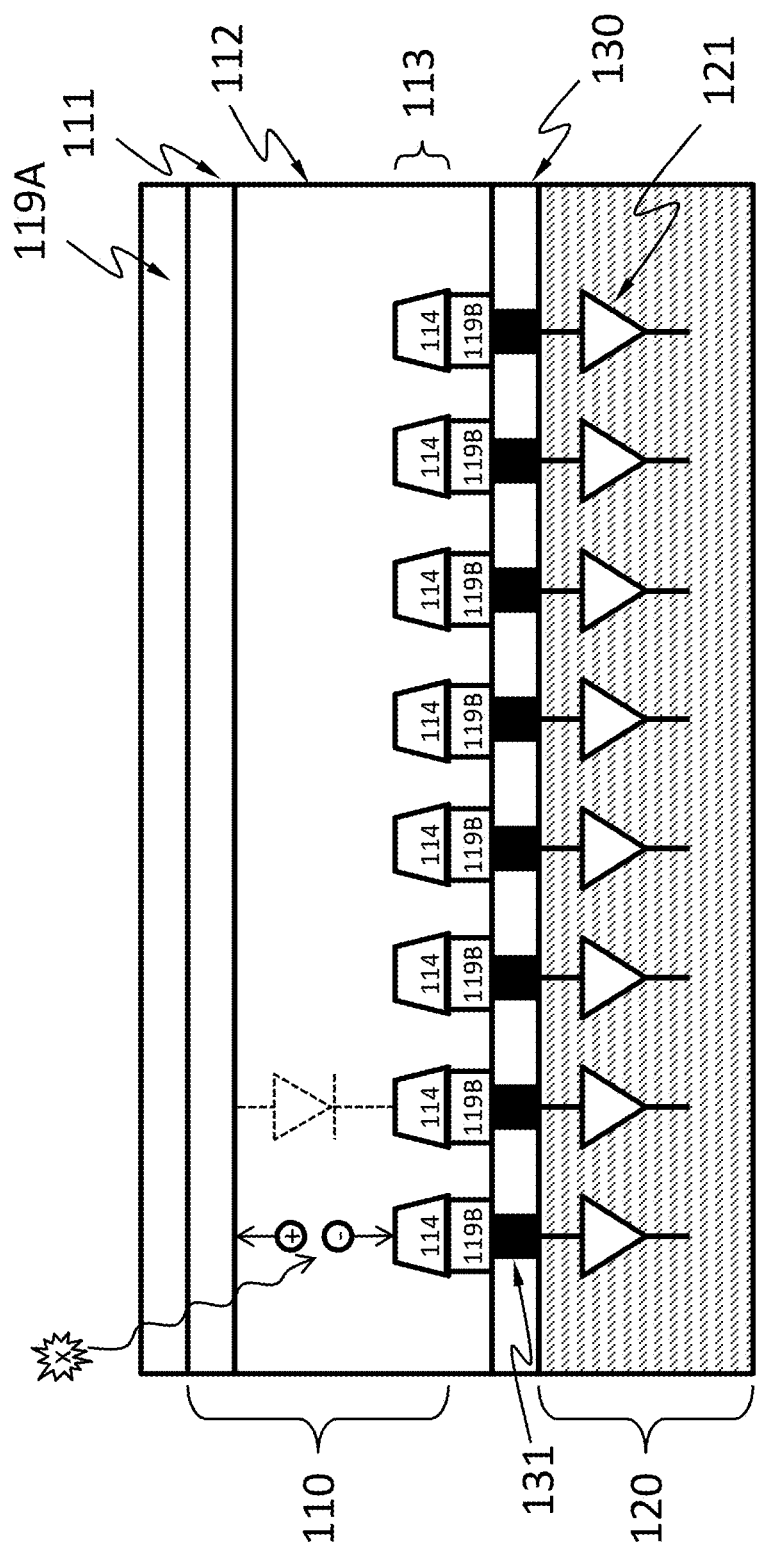
FIG. 6B schematically shows a detailed cross-sectional view of the X-ray detector, according to an embodiment.

As shown in a detailed cross-sectional view of the X-ray detector 100 in FIG. 6B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 6B, each of the discrete regions 114 of the second doped region 113 forms a diode with the first doped region 111 and the optional intrinsic region 112. Namely, in the example in FIG. 6B, the X-ray absorption layer 110 has a plurality of diodes having the first doped region 111 as a shared electrode. The first doped region 111 may also have discrete portions.

When X-ray from the X-ray source hits the X-ray absorption layer 110 including diodes, the X-ray photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single photon of the X-ray are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a photon of the X-ray incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a photon of the X-ray incident therein flow to the discrete region 114. Namely, less than 2%, less than 1%, less than 0.1%, or less than 0.01% of these charge carriers flow beyond the pixel.

Figure 6C:
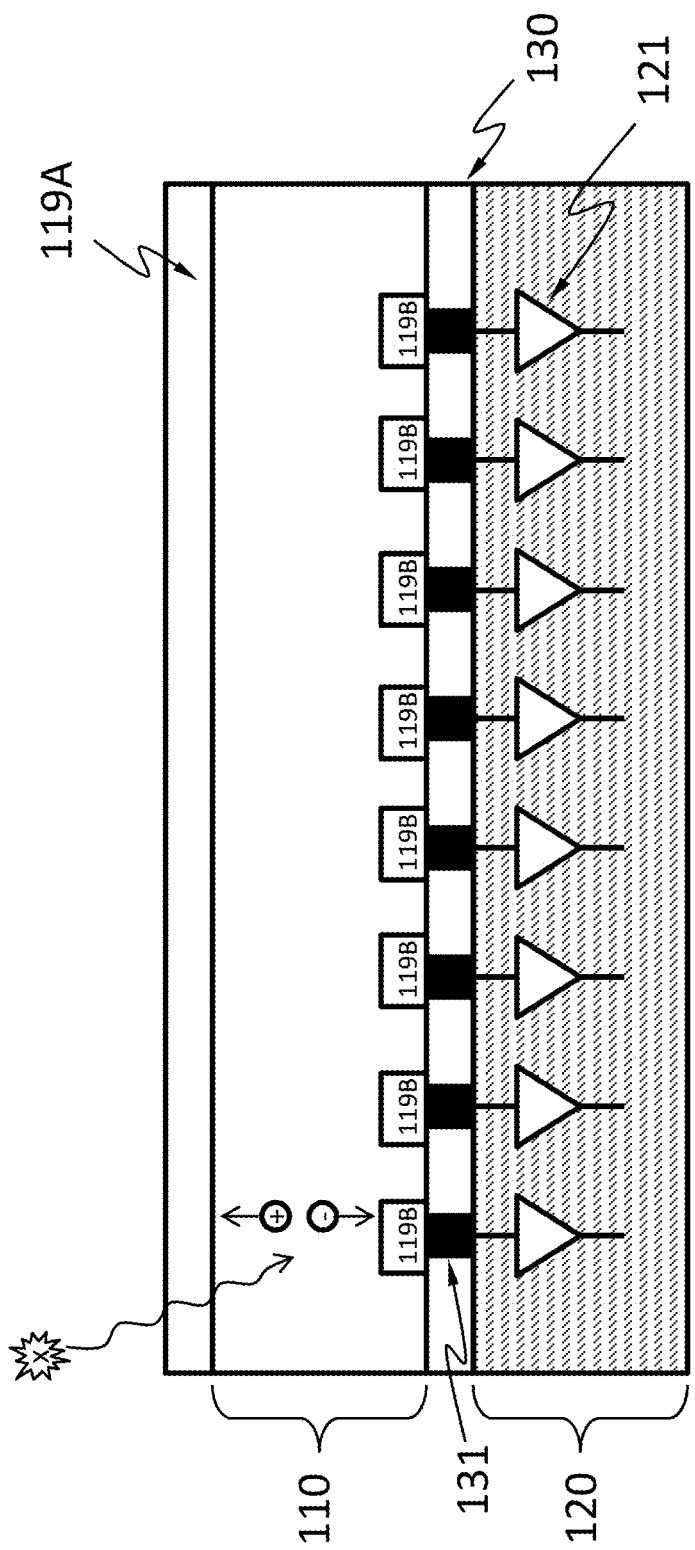
FIG. 6C schematically shows an alternative detailed cross-sectional view of the X-ray detector, according to an embodiment.

As shown in an alternative detailed cross-sectional view of the X-ray detector 100 in FIG. 6C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray of interest.

When the X-ray hits the X-ray absorption layer 110 including a resistor but not diodes, it may be absorbed and generate one or more charge carriers by a number of mechanisms. A photon of the X-ray may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single photon of the X-ray are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a photon of the X-ray incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a photon of the X-ray incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by the X-ray incident on the X-ray absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

The signals generated by the X-ray incident on the X-ray absorption layer 110 may be in a form of an electrical current. Likewise, the dark noise may also be in a form of an electrical current (e.g., a DC current flowing from the electric contacts 119B). If the current may be ascertained, the electrical current may be compensated for (e.g., diverted from) the electronic system 121.

Figure 7A:
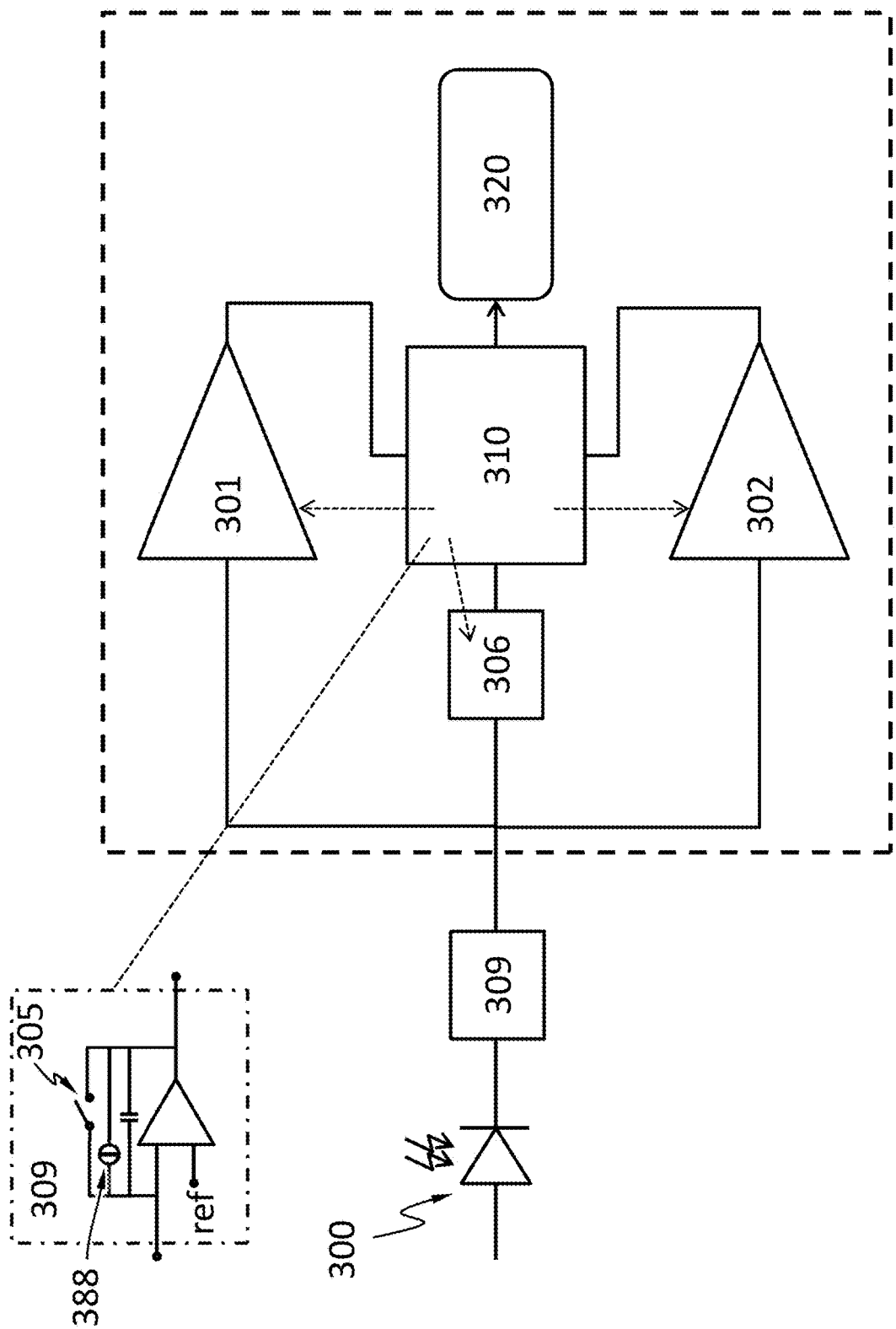
FIG. 7A and FIG. 7B each show a component diagram of an electronic system, according to an embodiment.
Figure 7B:
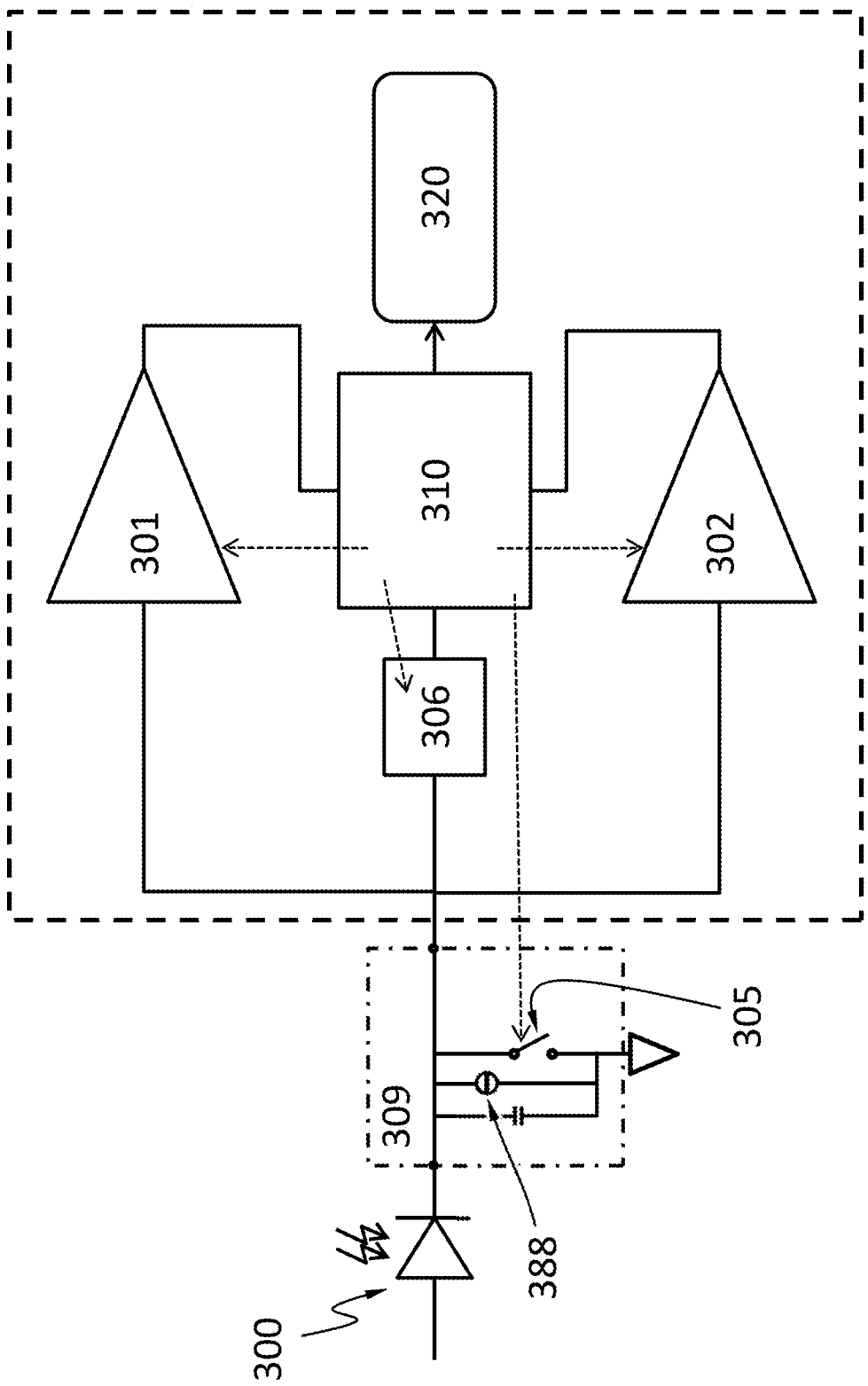

FIG. 7A and FIG. 7B each show a component diagram of the electronic system 121, according to an embodiment. The system 121 includes a capacitor module 309 electrically connected to an electrode of a diode 300 or an electrical contact, wherein the capacitor module is configured to collect charge carriers from the electrode. The capacitor module can include a capacitor and charge carriers from the electrode accumulate on the capacitor over a period of time ("integration period"). After the integration period has expired, the capacitor voltage is sampled and then reset by a reset switch. The capacitor module can include a capacitor directly connected to the electrode. The capacitor may be in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path.

In addition the capacitor module 309, which includes the current sourcing module 388, the electronic system 121 may further include a first voltage comparator 301, a second voltage comparator 302, a counter 320, a switch 305, a voltmeter 306 and a controller 310, as shown in FIG. 7A and FIG. 7B.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely $$|x| = \begin{cases} x, \text{if } x \geq 0 \\ -x, \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

The controller 310 may be configured to control the current sourcing module 388. For example, the controller 310 may change the magnitude of compensation for the dark noise by controlling the current sourcing module 388.

In an embodiment, the system 121 has no analog filter network (e.g., a RC network). In an embodiment, the system 121 has no analog circuitry.

The voltmeter 306 may feed the voltage it measures to the controller 310 as an analog or digital signal.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A method comprising:
acquiring a first image of an object inside a human or an animal with a first X-ray detector of an X-ray imaging system during an interventional radiology procedure on the human or the animal;

acquiring a second image of the object with the X-ray imaging system during the interventional radiology procedure, at a time later than acquiring the first image of the object;

determining a displacement of the first X-ray detector based on the first image and the second image; and moving the first X-ray detector by the displacement, with an actuator of the X-ray imaging system;

wherein the X-ray imaging system comprises the first X-ray detector, a second X-ray detector, the actuator;

wherein the first X-ray detector and the second X-ray detector are each capable of acquiring an image;

wherein a spatial resolution of the first X-ray detector is higher than a spatial resolution of the second X-ray detector;

wherein a detection area of the first X-ray detector is smaller than a detection area of the second X-ray detector;

wherein the actuator is configured to move the first X-ray detector relative to the second X-ray detector in one or more directions; and wherein one of the one or more directions is not perpendicular to an imaging plane of the second X-ray detector.

2. The method of claim 1, wherein the object is a portion of a catheter, a portion of a probe, a portion of a needle, or a portion of a wire.

3. The method of claim 1, wherein the object comprises a marker configured to show a contrast in the first image and the second image.

4. The method of claim 1, wherein determining the displacement of the first X-ray detector comprises subtracting a background from the first image or the second image, or comprises determining a differential between the first image and second image.

5. The method of claim 1, wherein acquiring the second image of the object with the X-ray imaging system comprises acquiring the second image by the first X-ray detector.

6. The method of claim 1, wherein acquiring the second image of the object with the X-ray imaging system comprises acquiring the second image by the second X-ray detector.

7. The method of claim 1, further comprising:
determining an area of interest containing the object by taking images with the second X-ray detector; and
moving the first X-ray detector to have the detection area of the first X-ray detector overlap with the area of interest.

8. The method of claim 7, wherein determining the area of interest containing the object comprises processing the images taken with the second X-ray detector.

9. The method of claim 1, further comprising:
making a composite image by combining an image formed by the first X-ray detector and another image formed by the second X-ray detector.

10. The method of claim 1, wherein the first X-ray detector is configured to count photons of X-ray incident thereon.

11. The method of claim 1, wherein the first X-ray detector is pixelated.

12. The method of claim 1, wherein the first X-ray detector comprises cadmium telluride (CdTe) or cadmium zinc telluride (CZT).

13. The method of claim 1, wherein the second X-ray detector comprises a scintillator.

14. The method of claim 1, wherein the actuator comprises a material that is selected from a group consisting of aluminum, aluminum composite, carbon fiber, and a combination thereof.

15. The method of claim 1, wherein the actuator comprises a robotic arm.

16. The method of claim 1, wherein the actuator comprises a first rail and a second rail; wherein the first X-ray detector is configured to slide along the first rail; and wherein the first rail is configured to slide along the second rail, wherein the first fail and the second rail are not parallel.

17. The method of claim 1, wherein the first X-ray detector comprises:
an X-ray absorption layer comprising an electrode;
a first voltage comparator configured to compare a voltage of the electrode to a first threshold;
a second voltage comparator configured to compare the voltage of the electrode to a second threshold;
a counter configured to register a number of X-ray photons absorbed by the X-ray absorption layer; and
a controller;
wherein the controller is configured to start a time delay from a time at which the first voltage comparator determines that an absolute value of the voltage of the electrode equals or exceeds an absolute value of the first threshold;
wherein the controller is configured to activate the second voltage comparator during the time delay;
wherein the controller is configured to cause the number of X-ray photons absorbed by the X-ray absorption layer registered by the counter to increase by one, if the second voltage comparator determines that an absolute value of the voltage of the electrode equals or exceeds an absolute value of the second threshold.

18. The method of claim 17, wherein the first X-ray detector further comprises a capacitor module electrically connected to the electrode, wherein the capacitor module is configured to collect charge carriers from the electrode.

19. The method of claim 17, wherein the controller is configured to activate the second voltage comparator at a beginning or an expiration of the time delay.

20. The method of claim 17, wherein the first X-ray detector further comprises a voltmeter, wherein the controller is configured to cause the voltmeter to measure the voltage of the electrode upon an expiration of the time delay.

21. The method of claim 17, wherein the controller is configured to determine an X-ray photon energy based on a value of the voltage of the electrode measured upon an expiration of the time delay.

22. The method of claim 17, wherein the controller is configured to connect the electrode to an electrical ground.

23. The method of claim 17, wherein a rate of change of the voltage of the electrode is substantially zero at an expiration of the time delay.

24. The method of claim 17, wherein a rate of change of the voltage of the electrode is substantially non-zero at an expiration of the time delay.

25. The method of claim 17, wherein the X-ray absorption layer comprises a diode.

26. The method of claim 17, wherein the first X-ray detector does not comprise a scintillator.

27. A computer program product comprising a non-transitory computer readable medium having instructions recorded thereon, the instructions when executed by a computer implementing a method comprising:

acquiring a first image of an object inside a human or an animal with a first X-ray detector of an X-ray imaging system during an interventional radiology procedure on the human or the animal;

acquiring a second image of the object with the X-ray imaging system during the interventional radiology procedure, at a time later than acquiring the first image of the object;

determining a displacement of the first X-ray detector based on the first image and the second image; and moving the first X-ray detector by the displacement, with an actuator of the X-ray imaging system;

wherein the X-ray imaging system comprises the first X-ray detector, a second X-ray detector, the actuator;

wherein the first X-ray detector and the second X-ray detector are each capable of acquiring an image;

wherein a spatial resolution of the first X-ray detector is higher than a spatial resolution of the second X-ray detector;

wherein a detection area of the first X-ray detector is smaller than a detection area of the second X-ray detector;

wherein the actuator is configured to move the first X-ray detector relative to the second X-ray detector in one or more directions; and wherein one of the one or more directions is not perpendicular to an imaging plane of the second X-ray detector.

* * * * *